United States Patent
Cowgill

(10) Patent No.: US 7,685,885 B2
(45) Date of Patent: Mar. 30, 2010

(54) MANIPULATOR CONSTANT FORCE SPRING COUNTERBALANCE

(75) Inventor: Bruce L. Cowgill, Newbury Park, CA (US)

(73) Assignee: Teradyne, Inc., North Reading, MA (US)

( * ) Notice: Subject to any disclaimer, the term of this patent is extended or adjusted under 35 U.S.C. 154(b) by 0 days.

(21) Appl. No.: 11/953,744

(22) Filed: Dec. 10, 2007

(65) Prior Publication Data

US 2009/0145241 A1    Jun. 11, 2009

(51) Int. Cl.
*G01N 3/08* (2006.01)

(52) U.S. Cl. .......................................... 73/828; 73/760

(58) Field of Classification Search ............ 73/760–828
See application file for complete search history.

(56) References Cited

U.S. PATENT DOCUMENTS

| | | | | |
|---|---|---|---|---|
| 3,863,544 | A | * | 2/1975 | Reeber et al. ............... 409/89 |
| 4,230,205 | A | * | 10/1980 | Darwent .................... 187/265 |
| 4,449,885 | A | | 5/1984 | Hertel et al. |
| 4,705,447 | A | | 11/1987 | Smith |
| 4,721,424 | A | | 1/1988 | Aldridge et al. |
| 4,781,156 | A | * | 11/1988 | Berger et al. ............. 123/192.1 |
| 4,943,020 | A | | 7/1990 | Beaucoup et al. |
| 4,973,015 | A | | 11/1990 | Beaucoup et al. |
| 5,163,649 | A | | 11/1992 | Schehr |
| 5,209,325 | A | * | 5/1993 | Gines et al. .................... 188/67 |
| 5,818,219 | A | * | 10/1998 | Hama et al. ............. 324/158.1 |
| 6,133,726 | A | * | 10/2000 | Heigl ....................... 324/158.1 |
| 6,239,573 | B1 | * | 5/2001 | Schmall ........................ 318/687 |
| 6,352,593 | B1 | | 3/2002 | Brors et al. |
| 6,558,506 | B1 | | 5/2003 | Freeman et al. |
| 6,621,680 | B1 | | 9/2003 | Segervall |
| 6,645,116 | B1 | | 11/2003 | Usoro et al. |
| 6,790,125 | B2 | | 9/2004 | Kane et al. |
| 6,828,774 | B2 | | 12/2004 | Bosy et al. |
| 6,852,629 | B2 | | 2/2005 | Kane et al. |
| 6,888,343 | B1 | | 5/2005 | Holt et al. |
| 7,245,118 | B2 | | 7/2007 | Holt et al. |
| 7,424,997 | B2 | * | 9/2008 | Achtari et al. ............... 254/278 |
| 2004/0112760 | A1 | | 6/2004 | Basol et al. |
| 2005/0101451 | A1 | * | 5/2005 | Ooka .......................... 482/99 |

OTHER PUBLICATIONS

Small Parts, Inc.; Spring, Constant Force—Stainless Steel Type 301 webpage; printed Nov. 12, 2007; available at http://www.smallparts.com/products/descriptions/cfs.cfm.

* cited by examiner

*Primary Examiner*—Max Noori
(74) *Attorney, Agent, or Firm*—Christopher R. Balzan

(57) ABSTRACT

In various embodiments, a test head weight compensation device includes at least one constant force spring connected between a test head assembly of the automated test equipment system and a test head supporting structure to apply a constant supportive force to the test head assembly. The at least one constant force spring is mounted to the test head supporting structure with a distal end of the constant force spring is attached to the test head assembly. Alternately, the constant force spring is mounted to the test head assembly with the distal end of the constant force spring connected to the test head supporting structure. The test weight compensation device may include pulleys attached to the supporting structure or the test head assembly with the constant force spring passed through the pulley to multiply the force of the constant force spring.

22 Claims, 8 Drawing Sheets

MANIPULATOR CONSTANT FORCE SPRING COUNTERBALANCE

BACKGROUND

In Automatic Test Equipment (ATE) systems, a test head generally contains the massive volume of electronic circuits and cabling, mechanical packaging, and cooling hardware necessary for testing integrated circuit wafers and packaged chips during and after manufacturing processes. As integrated circuits have become increasingly dense, the automatic test equipment systems that evaluate functionality and performance of integrated circuit devices must be able to fit higher numbers of communication pathways or channels on the instrumentation boards for providing stimulus signals and receiving response signals to and from the integrated circuit devices under test. These higher circuit densities have lead to increasing connection densities and increasingly higher power densities within the circuits of the automatic test equipment systems. Further, the lower delay times and the higher clock rates have created signals that must be transmitted on coaxial cables or equivalent high speed cabling. The performance requirements of integrated circuits have forced the use of one or more coaxial cables to the device-under-test. Further, these requirements have even forced the use of coaxial cables with larger conductors. The coaxial cable bundles are physically long, wide, and heavy, with a volume of several thousand 2-foot coaxial cables. To fulfill these test head requirements, test heads now have a weight of greater than 1000 lbs (452 kg).

SUMMARY

In an automated test equipment system, some embodiments of a test head weight compensation device include at least one constant force spring connected between a test head assembly of the automated test equipment system and a test head supporting structure. The constant force spring applies a constant supportive force to the test head assembly along a full range of vertical travel of the test head assembly. The constant supportive force has substantially the same magnitude and opposite direction as a weight of the test head assembly.

In one embodiment, the at least one constant force spring is mounted to the test head supporting structure. A distal end of the at least one constant force spring is attached to the test head assembly. In another embodiment, the at least one constant force spring is mounted to the test head assembly and the distal end of the at least one constant force spring connected to the test head supporting structure.

In other embodiments the test head weight compensation further incorporates at least one pulley connected to the test head assembly. The at least one constant force spring is mounted to the support structure and the distal end passes through the at least one pulley. The distal end is then connected to the supporting structure. The at least one pulley may be connected to the test head or to a test head support arm of the test head assembly.

In some embodiments, the test head weight compensation device further incorporates at least one pulley connected to the supporting structure. The at least one constant force spring is mounted in these embodiments to the test head assembly with the distal end of the at least one constant force spring connected to the test head assembly.

In various embodiments of automatic test equipment systems, a manipulator for supporting and orienting a test head has a weight compensation device connected between the test head assembly and a supporting structure of the manipulator. The weight compensation device applies an upwardly directed constant force along a range vertical motion of the test head assembly to offset the weight of the test head assembly. The weight compensation device includes at least one constant force spring mounted to the supporting structure. A distal end of the constant force spring is connected to support the test head assembly so as to substantially reduce a force necessary to overcome the inertia of the test head.

In various embodiments, the manipulator further incorporates at least one pulley connected to the test head. The distal end of the at least one constant force spring passes the through the at least one pulley before connection to supporting structure. The at least one pulley multiplies the force of the constant force spring applied to compensate the weight of the test head. In alternate embodiments, the at least one pulley is attached to a support arm of the test head assembly. The support arm holding the test head. The support arm rests in a guide rail of the supporting structure to direct the movement of the test head assembly.

In some embodiments the manipulator further provides wheels mounted to the manipulator so as to allow the manipulator to be mobile.

In various embodiments, a mobile test head manipulator is capable of supporting and orienting a test head. The mobile test head manipulator includes at least one constant force spring. The constant force spring is connected between a test head assembly and a test head supporting structure for applying a constant supportive force to the test head assembly along a range of vertical travel of the test head assembly. The constant supportive force has substantially the same magnitude and opposite direction as a weight of the test head assembly. The mobile test head manipulator further includes wheels secured to a base of the manipulator to provide the mobility.

In various embodiments, the at least one constant force spring is mounted to the supporting structure with a distal end of the at least one constant force spring attached to the test head assembly. In alternate embodiments, the at least one constant force spring is mounted to the test head assembly with a distal end of the at least one constant force spring attached to the supporting structure.

In some of those embodiments where the at least one constant force spring is mounted to the test head supporting structure, the mobile test head manipulator further includes at least one pulley connected to the test head assembly. The constant force spring passes through the at least one pulley with the distal end of the constant force spring connected to the test head supporting structure. The at least one pulley may be mounted to the test head itself or to a support arm of the test head assembly.

In some of those embodiments where the at least one constant force spring is mounted to the test head assembly, the mobile test head manipulator further includes at least one pulley connected to the test head supporting structure. The constant force spring passes through the at least one pulley with the distal end of the constant force spring connected to the test head assembly.

The test head support arm of the test head assembly rests in a guide rail of the test head supporting structure.

DESCRIPTION

Figure 1A:
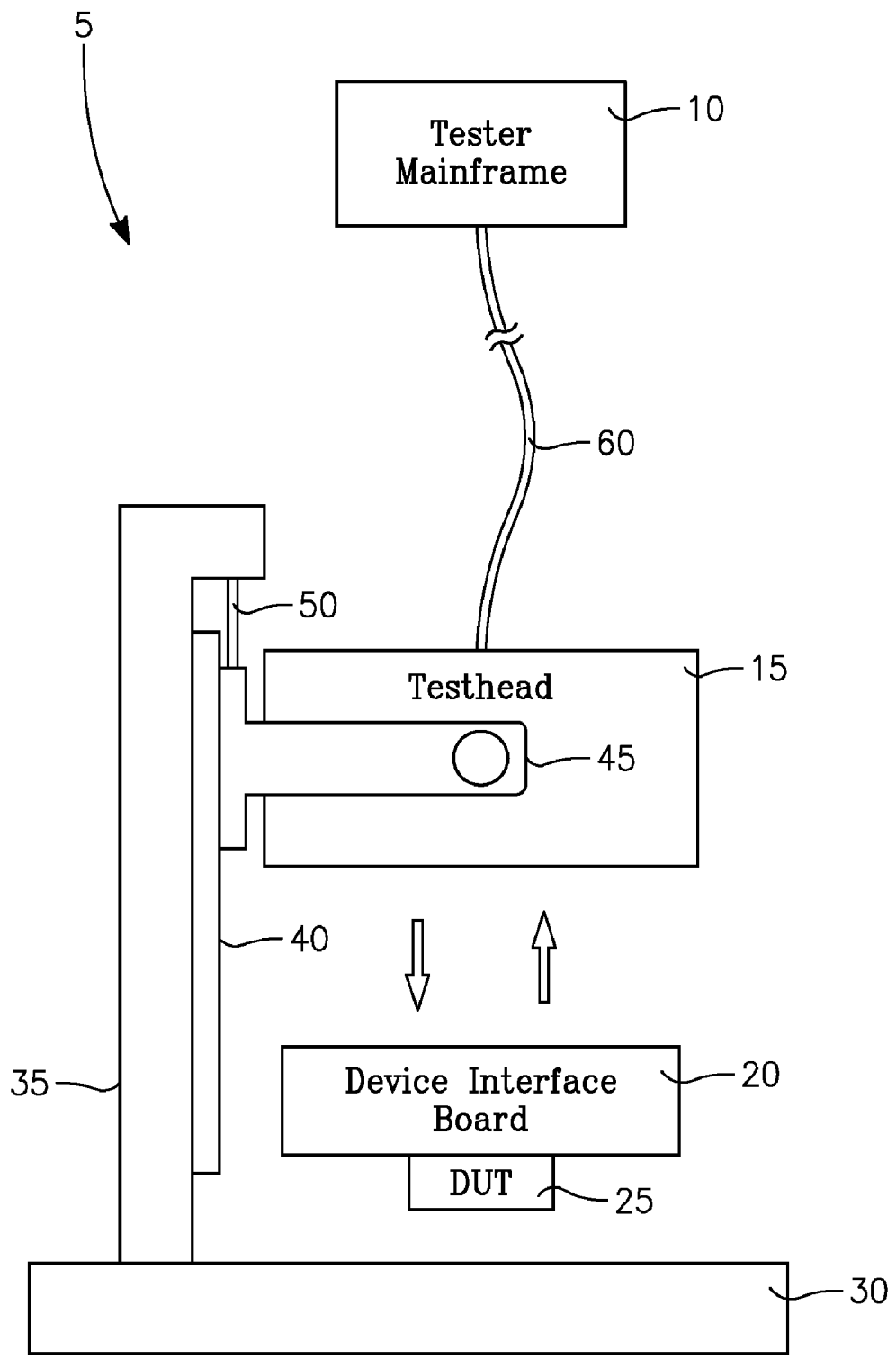
FIGS. 1A, 1B, and 1C are simplified diagrams of a side view of automatic test equipment systems showing a manipulator controlling the vertical positioning of a test head with respect to a device-under-test.
Figure 1B:
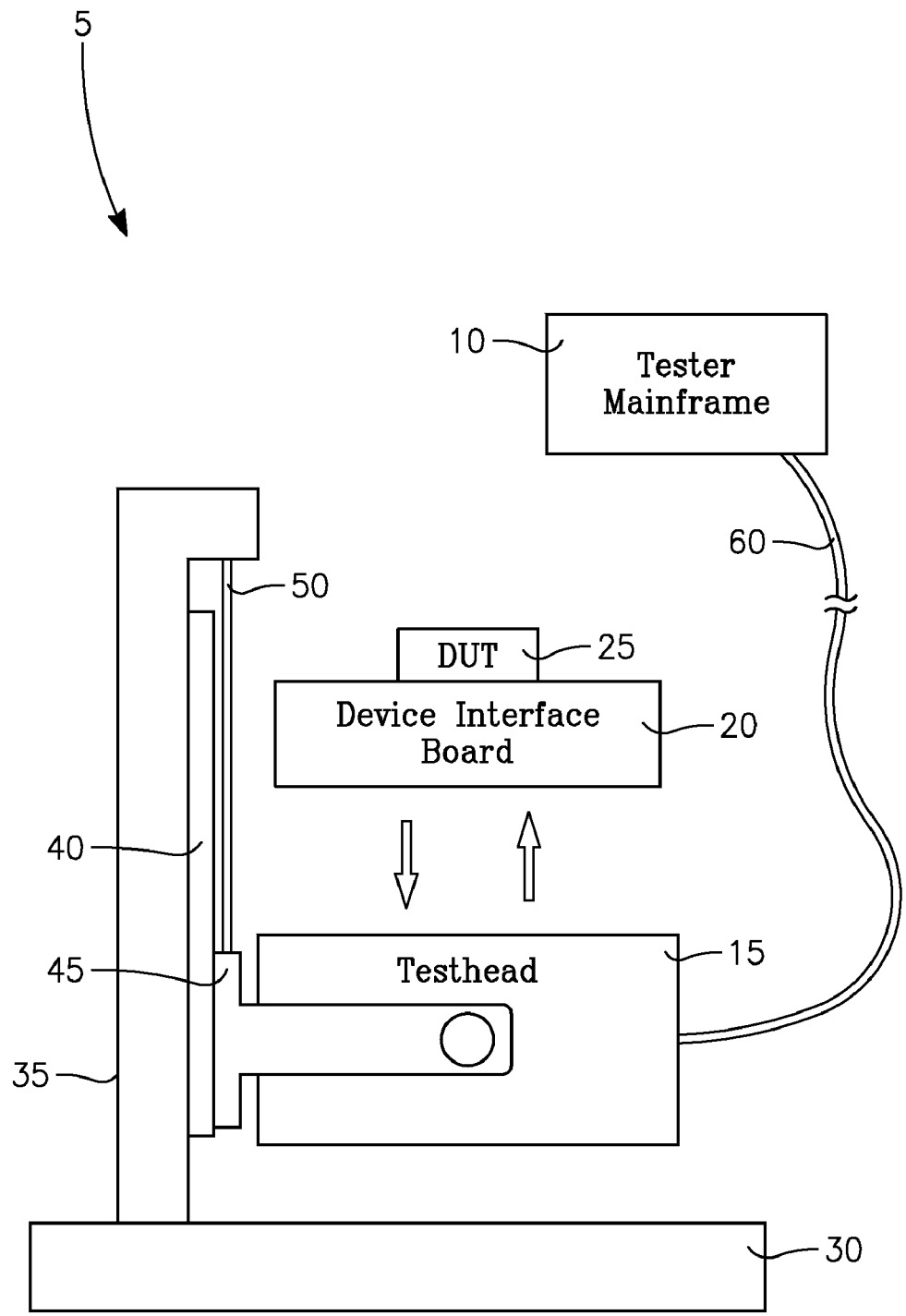
Figure 1C:
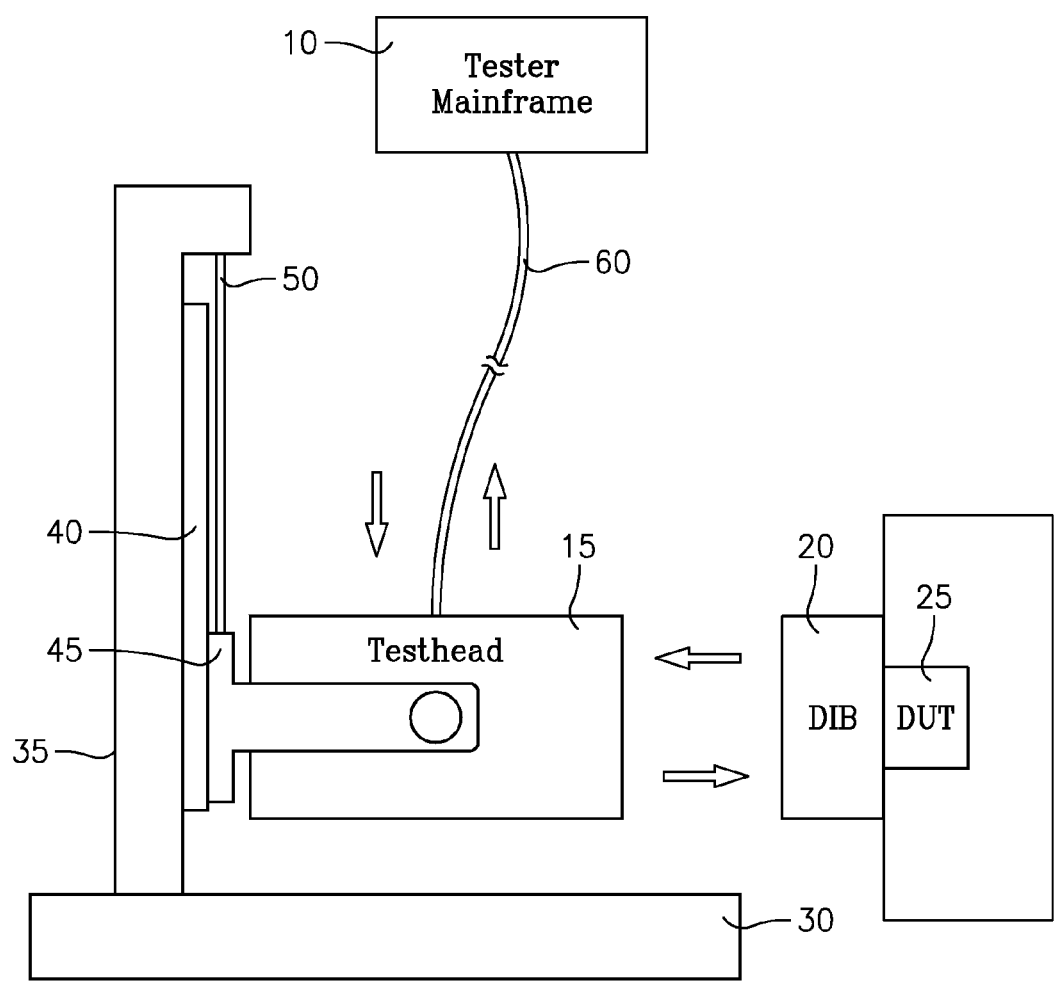

An automatic test equipment system 5, as shown in FIGS. 1a, 1b, and 1c has a tester mainframe 10 that is in communication with a test head 15 through the communication cabling 60. The test head 15 is to be placed in contact with a device interface board (DIB) 20. In some embodiments, signals from the test head 15 may be routed to the device interface board 20 through a translator (not shown). In operation, the device interface board 20 is electrically connected to a device-under-test (DUT) 25 for testing the device-under-test 25. For example, the automated test equipment (ATE) system 5 may be for testing integrated circuits, and the device-under-test 25 may be a semiconductor device including an integrated circuit. As described above, signals from the test head 15 may be routed through cables (not shown) to the device interface board 20.

The tester mainframe 10 includes circuitry for generating test signals and evaluating test signals. The tester mainframe 15 sends test signals to the device-under-test 25 and receives test signals from the device-under-test 25 through the test head 15 and the device interface board 20. The device-under-test 25 may be a packaged silicon die including an integrated circuit to be tested. In another embodiment, the interface board 20 is a probe interface board, and the device-under-test 25 may be a semiconductor wafer including an integrated circuit to be tested.

A test head 15 must be aligned on multiple axes for providing a precise connection with the device-under-test 25 that includes a integrated circuit wafer probe station for wafers or a device handler for packaged individual chips. The test head 15 has alignment devices to insure this precise alignment. To adjust the placement of the test head 15, a manipulator 30 secures the test head 15 and provides the necessary precise movement of the test head 15 in the vertical, horizontal, and the rotational axis to appropriately align the test head 15 with the probe station or the device handler holding the device-under-test 25.

For vertical control of a test head 15, manufacturers of manipulators 30 for test heads of the prior art employ several devices for counterbalancing the weight of the test head. The prior art devices include electric motors, pneumatic and hydraulic rams, and rope and pulley system with a counter-balancing weight. In applications where the test head 15 must be sufficiently portable to be moved between test probe stations and device handlers, the manipulator 30 must movable.

The weight of the electric motors, pneumatic and hydraulic rams, or the rope and pulley system with the counter balancing weight is undesirable.

As described above, the test head 15 has a large mass of greater than 1000 lbs. (452 kgs.) and must be supported by a manipulator 30. The manipulator has a support structure 35 that provides a vertical support for the test head 15. The support structure has a guide rail 40 into which a support arm 45 mounted. The support arm 45 is not secure in the vertical direction and is permitted to slide within the confines of the guide rail 40.

Figure 2:
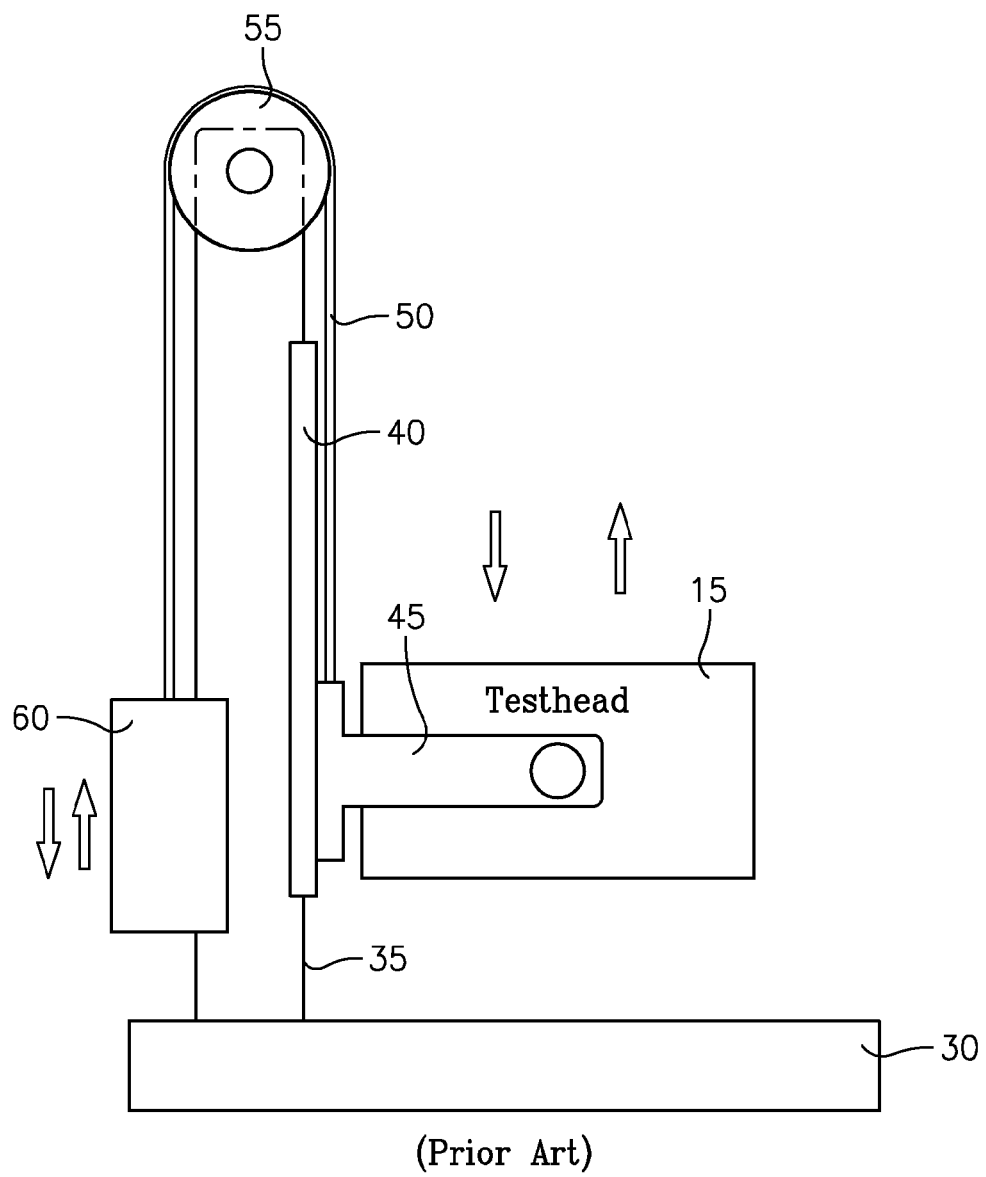
FIG. 2 is a simplified diagram of a side view of a manipulator of the prior art controlling a test head using a rope and pulley system with a counter balancing weight.

A cable, wire rope, or similar fastening device 50 is connected from the support structure 35 to the test head 15 through the support arm 45. In the prior art, as shown in FIG. 2, the cable 50 is passed through a pulley 55 to the weights 60. The pulley 55 is attached to the support structure by a process such as welding. The weights 60 are adjusted to counterbalance the weight of the test head 15 such that the test head 15 may be moved with minimal force. It should be noted that in this instance the manipulator 30 must now support not only the weight of the test head 15 but also the load of the weights 60.

The present inventor has discovered that what is needed is a weight compensation device with relatively low mass that is connected between a test head 15 within an automatic test equipment system 5 and a supporting structure 35 of a manipulator 30 to compensate for the weight of the test head 15.

Referring to FIG. 1a, the device interface board 20 is connected to be in contact with the device-under-test 25. The device-under-test being a probe station of an integrated circuit wafer or a device handler for packaged integrated circuit chips. In this example the test head 15 is to be lowered to make contact with the device interface board 20. It should be noted that the device interface board 20 may be connected to the test head 15 and lowered with the test head 15 to make contact with the device-under-test 25.

In FIG. 1b, the test head 15 is to be raised to make contact with the device interface board 20. As noted above, the device interface board 20 may be connected to the test head 15 and raised with the test head 15 to make contact with the device-under-test 25.

In FIG. 1c, the test head 15 is to be is moved horizontally to make contact with the device interface board 20. The vertical motion of the test head 15 is required for insuring alignment of the test head 15 with the device interface board 20 for insuring precise connection.

Figure 3:
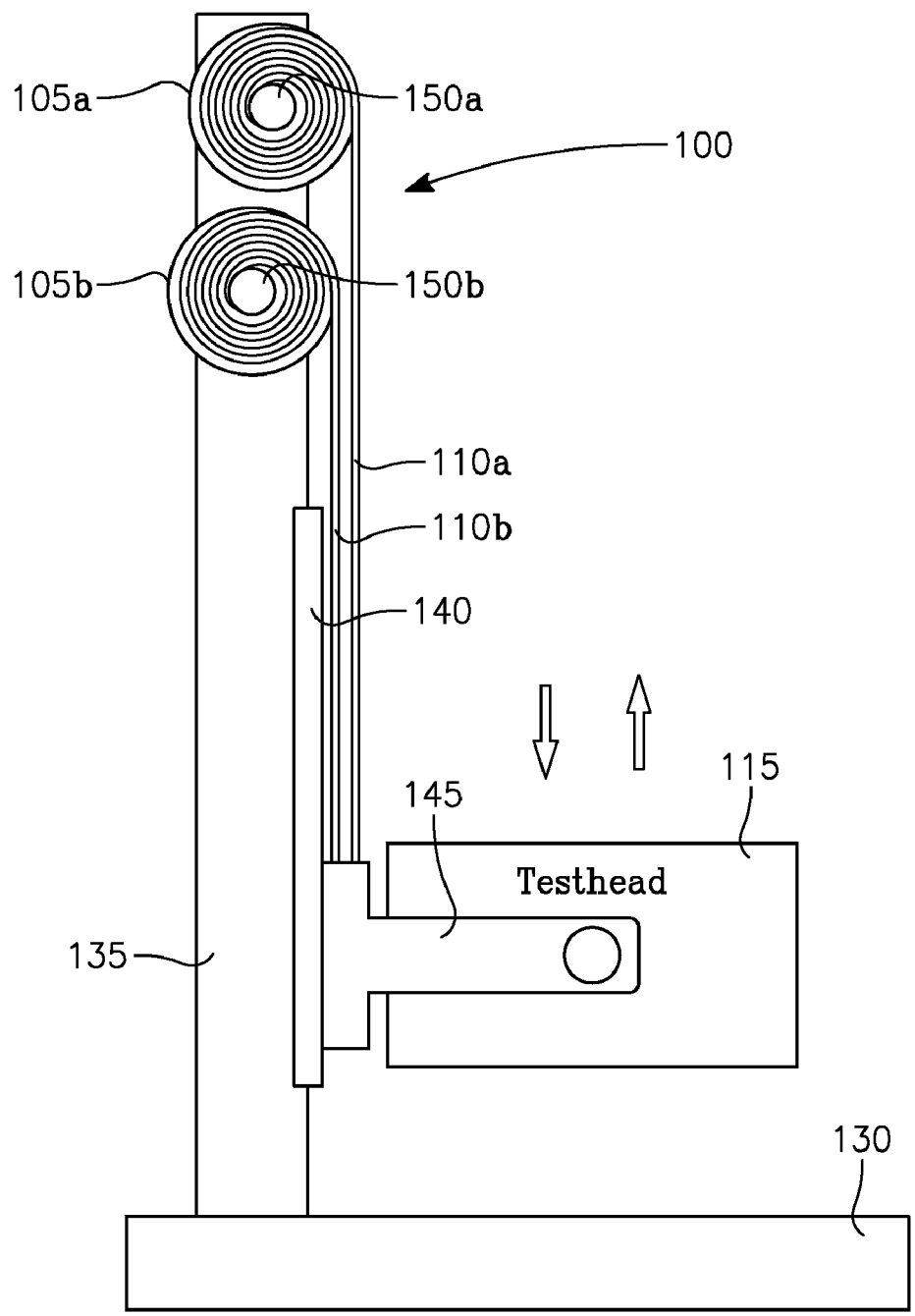
FIG. 3 is a simplified diagram of a side view of an embodiment of a manipulator for controlling a test head using a constant force spring for compensating for the weight of the test head.

Refer now to FIG. 3 for one embodiment of a weight compensation device 100 for connecting a test head 115 within an automatic test equipment system to a supporting structure 135 of a manipulator 130 for applying an upwardly directed force to the supporting structure 135 to offset the weight of the test head 115. The weight compensation device 100 includes constant force springs 105a and 105b having one end attached to the supporting structure 135 and connected to inhibit the test head 115 from moving vertically unless a relatively small external force is applied.

The constant force springs 105a and 105b have one end in contact with the freely rotating drums 150a and 150b respectively, which are attached to the support structure 135, and a distal end connected to support the test head 115. The distal end of the constant force springs 105a and 105b may be attached directly to the test head (not shown). Alternately, the test head 115 is mounted to the support arm 145 and the constant force springs 105a and 105b are connected to the support arm 145 to bear the weight of the test head 115. The support arm 145 is mounted to the guide rails 140 that are secured to the support structure 135. The support arm 145 rides vertically within the guide rails 140 for placement of the test head 115 during vertical positioning.

The constant force springs 105a and 105b are known in the art and are springs that exert a constant force over its full range of operational motion. Constant force springs do not obey Hooke's law and are constructed as rolled ribbons or strips 110a and 110b of spring steel or pre-stressed stainless steel such that the spring is relaxed when it is fully rolled up. The roll of the steel strips 110a and 110b exerts a nearly constant restraining force to resist uncoiling. When the strip 110a and 110b is extended, the inherent stress resists the loading force at a nearly constant rate. The steel strips 110a and 110b have relatively unlimited travel length as long as approximately 1½ wraps remain on the freely rotating drums 150a and 150b at maximum extension of the constant force springs 105a and 105b.

The steel strips 110a and 110b are mounted on a freely rotating drum 150a and 150b, respectively. The drum diameter should be 10 to 20% larger than the natural diameter of the coiled steel strip 110a and 110b. One and one-half wraps should remain on the drum 150a and 150b at maximum extension. The geometry of the steel strip 110a and 110b and the 150a and 150b drum 150a and 150b are constructed to provide the force necessary to compensate for the weight of the test head 115 such that the test head maintains a vertically nonmoving equilibrium position. In various embodiments, the constant force springs 105a and 105b provide a supportive force having substantially a same magnitude and opposite direction as the weight of the test head assembly (the test head 115 and support arm 145). A relatively small force is applied to the test head 115 that is sufficient to overcome the inertia of the test head 115 to cause the test head 115 to move vertically to contact the device interface board 20 of FIGS. 1a, 1b, and 1c. The constant force springs 105a and 105b are the types of constant force or negator springs as manufactured by Associated Spring, Farmington, Conn. or Vulcan Spring, Telford, Pa.

The amount of supportive force will vary in different embodiments, depending on the weight of the test head, and the amount of friction in the system. Ideally, in a frictionless or near frictionless system, the constant force springs 105a and 105b would provide sufficient counterbalance force so that less than one pound of force would be sufficient to move or stop the test head 115. In one specific embodiment with friction, the constant force spring(s) provide(s) sufficient counter balance force, so that the force required to overcome the static friction of the test head has a value in a range from about twenty to about forty pounds of force, for example. This value(s) will vary depending on the difference between the static and dynamic friction. In some frictional embodiments the value to overcome the static friction may be less. In some frictional embodiments the value to overcome the static friction may be greater.

Figure 4:
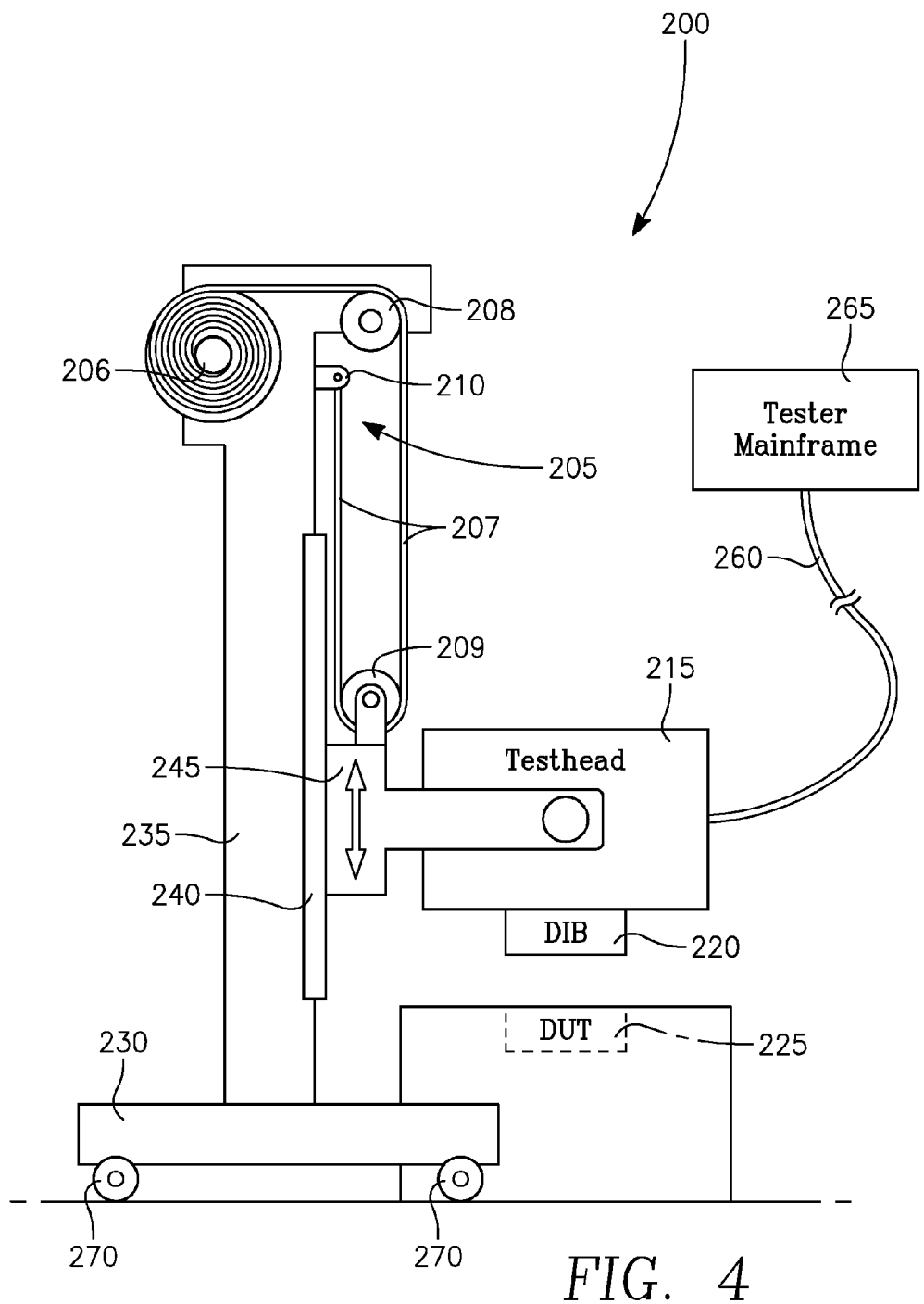
FIG. 4 is a simplified diagram of a side view of another embodiment of a manipulator for controlling a test head using a constant force spring for compensating for the weight of the test head.

Refer now to FIG. 4 for another embodiment of an automated test equipment system. An automatic test equipment system 200, as shown in FIG. 1a, 1b, or 1c has a tester mainframe 265 that is in communication with a test head 215 through the communication cabling 260. In the embodiment of FIG. 4 the device interface board (DIB) is mounted directly to the test head 215. The device interface board (DIB) 220 is then physically brought with the test head 215 to contact the device-under-test 225. In some embodiments, signals from the test head 215 may be routed to the device interface board 220 through a translator (not shown). In operation, the device interface board 220 is electrically connected to a device-under-test (DUT) 225 for testing the device-under-test 225.

The tester mainframe 265 includes circuitry for generating test signals and evaluating test signals. The tester mainframe 265 sends test signals to the device-under-test 225 and receives test signals from the device-under-test 225 through the test head 215 and the device interface board 220. The device-under-test 225 may be a packaged silicon die including an integrated circuit to be tested. In another embodiment, the interface board 220 is a probe interface board, and the device-under-test 225 may be a semiconductor wafer including an integrated circuit to be tested.

As described above, the test head 215 has a large mass of greater than 1000 lbs. (452 kg) and must be supported by the manipulator 230. The manipulator has a support structure 235 that provides a vertical support for the test head 215 through the weight compensation device 205. The support structure 235 has a guide rail 240 into which a support arm 245 mounted. The support arm 245 is not secure in the vertical direction and is permitted to slide within the confines of the guide rail 240. The support arm 245 and the test head 215 together form a test head assembly. Although not shown, the support arm 245 and the test head 215 may move with respect to each other, in some embodiments.

The weight compensation device 205 includes a constant force spring 207 having one end in contact with a freely rotating drum 206 attached to the supporting structure 235. The outer end of the constant force spring 207 coil is passed through the pulley 208 that is secured to the supporting structure 235. The outer end of the constant force spring 207 coil is then fed through the pulley 209. The pulley 209 is secured to the support arm 245 and the outer end or distal end of the constant force spring 207 coil is then secured by the attachment point 210 to supporting structure 235. The pulley 209 provides mechanical advantage that multiplies the force of the constant force spring 207 applied to the support arm 245 to compensate the weight of the test head 215. It should be noted that the pulley 209 is shown as connected to the support arm 245, but is equally in keeping with the intent of this invention to attach the pulley 209 directly to the test head 215 to inhibit the test head 215 from moving vertically unless a relatively small external force is applied.

In some embodiments, multiple pulleys (not shown) in a block and tackle arrangement may be included. In some of such embodiments, the constant force spring 207 could be fed through a pulley (not shown) attached to the supporting structure 235 and the distal end of the constant force spring 207 could be connected to the attachment point 210, or to the test head assembly, i.e. the test head 215 or support arm 245.

As used herein, the term pulley refers to a device to provide mechanical advantage to multiply the force of the constant force spring, or to change the direction of the force, such as for example bearings, axles, low friction guides, or the like.

The manipulator 230 of this embodiment supports only the weight of test head assembly, which includes the test head 215 and the support arm 245 and does not have to support the load of weights as in the prior art. This allows a base of the manipulator 230 be mounted on wheels 270. With the wheels 270, the manipulator 230 is now mobile and is now movable to integrated circuit wafer probe stations for probing wafers or to device handlers for testing packaged individual chips.

Figure 5:
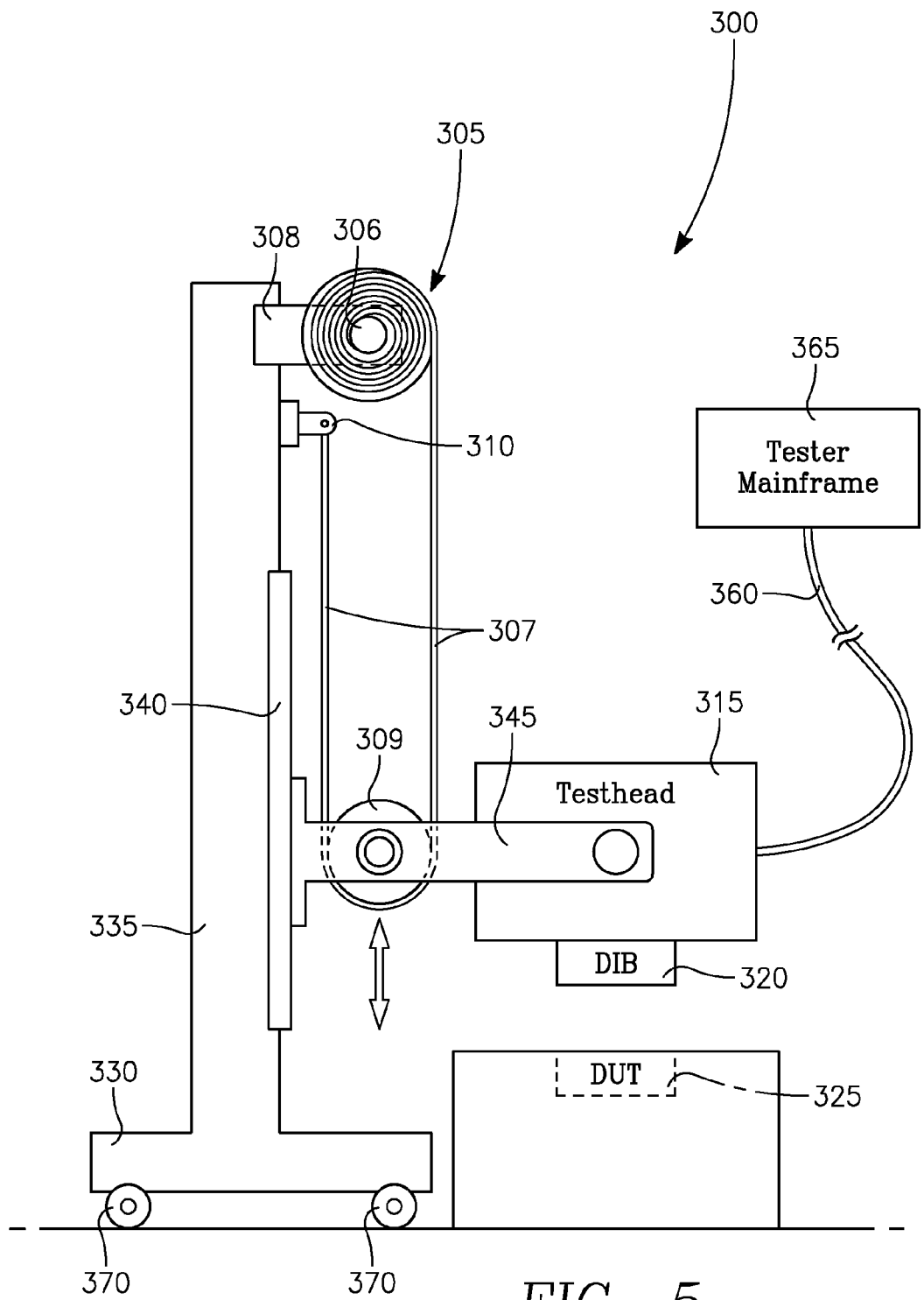
FIG. 5 is a simplified diagram of a side view of a third embodiment of a manipulator for controlling a test head using a constant force spring for compensating for the weight of the test head.

Refer now to FIG. 5 for discussion of another implementation of the weight compensation device 305 within an automatic test equipment system 300. The weight compensation device 305 connects a test head 315 to a supporting structure 335 of a manipulator 330 for applying an upwardly directed force to the support structure 335 to offset the weight of the test head 315. The test head 315 with the attached device interface board 320 is raised and lowered to be connected to the device-under-test 325.

The weight compensation device 305 is attached to the support structure 335 through the bracket 308. The weight compensation device 305 includes a constant force spring 307 having one end in contact with a freely rotating drum 306 that is attached to the supporting structure 335. The freely rotating drum 306 is mounted to the bracket 308 that is attached to the support structure 335.

A outer end of the constant force spring 307 coil is then fed through the pulley 309 and the outer end of the constant force spring 307 is then secured by the attachment point 310 to support structure 335. The pulley 309 is secured to the support arm 345. The pulley 309 increases the mechanical advantage or multiplies the force of the constant force spring 307 applied to the support arm 345 to compensate the weight of the test head 315. It should be noted that the pulley 309 is shown as connected to the support arm 345, but could be attached directly to the test head 315 to inhibit the test head 315 from moving vertically unless a relatively small external force is applied.

The manipulator 330 of this embodiment supports only the weight of the test head 315, including the support arm 345 and does not have to support the load of weights as in the prior art. This allows the manipulator 330 be mounted on wheels 370. With the wheels 370, the manipulator 330 is now mobile and is movable to integrated circuit wafer probe stations for probing wafers or to device handlers for testing packaged individual chips.

Figure 6:
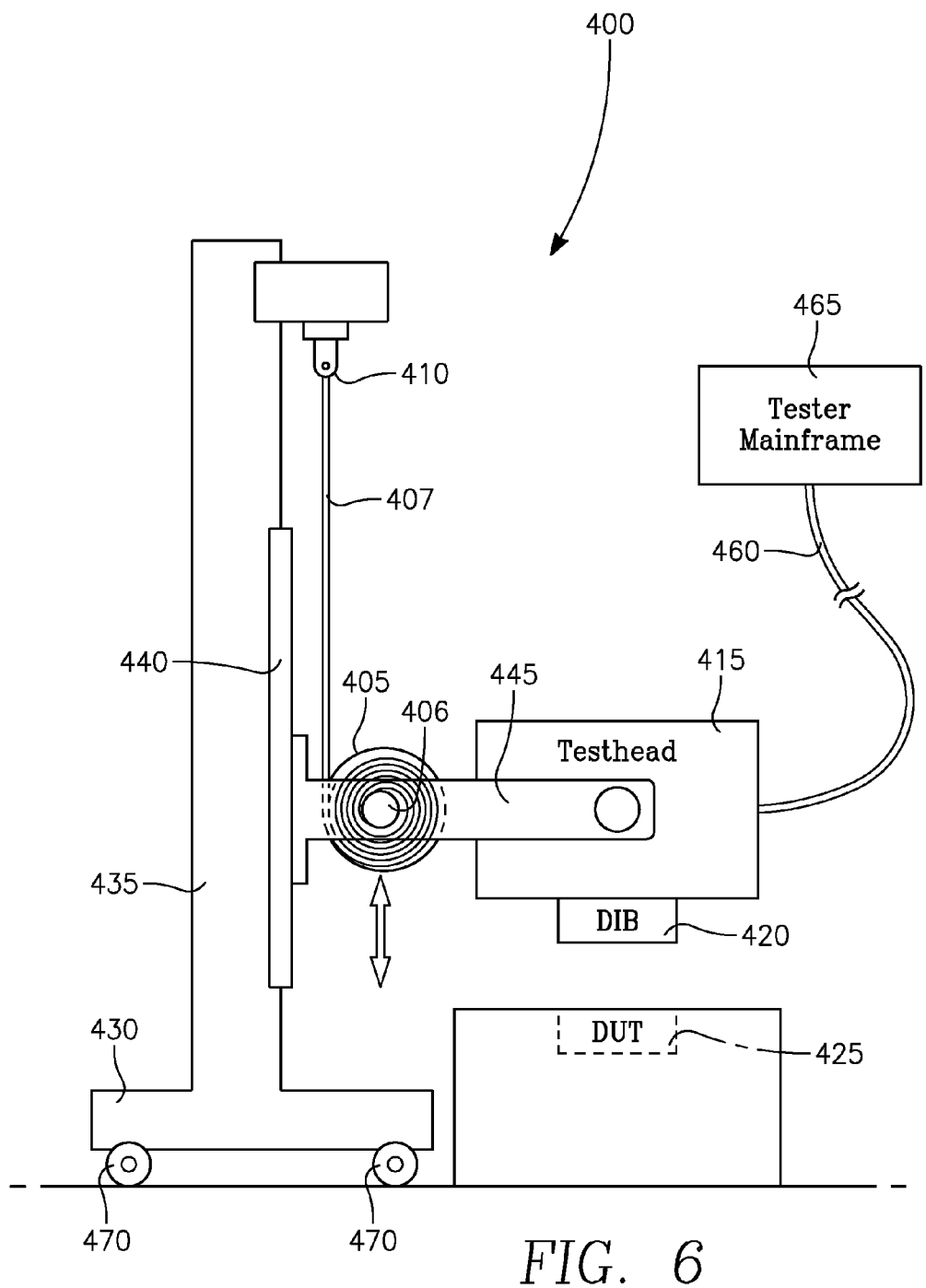
FIG. 6 is a simplified diagram of a side view of another embodiment of a manipulator for controlling a test head using a constant force spring for compensating for the weight of the test head.

Refer now to FIG. 6 for discussion of another implementation of the weight compensation device 405 within an automatic test equipment system 400. The weight compensation device 405 between a test head 415 and a supporting structure 435 of a manipulator 430 for applying an upwardly directed constant force to the support structure 435 to offset the weight of the test head 415. The test head 415 with the attached device interface board 420 is raised and lowered to be connected to the device-under-test 425.

The weight compensation device 405 is mounted to the support arm 445. The weight compensation device 405 includes a constant force spring 407 having one end in contact with a freely rotating drum 406 that is mounted to the supporting arm 445. An outer end or distal end of the constant force spring 407 coil is secured by the attachment point 410 to the support structure 435. The nearly constant force of the constant force spring 407 is applied to the support arm 445 to compensate the weight of the test head 415. It should be noted that the constant force spring 409 is shown as connected to the support arm 445, but could be attached directly to the test head 415 to inhibit the test head 415 from moving vertically unless a relatively small external force that is sufficient to overcome the inertia of the test head 415 is applied.

As described above, the manipulator 430 of this embodiment supports only the weight of the test head 415, including the support arm 445 and does not have to support the load of weights as in the prior art. This allows the manipulator 430 be mounted on wheels 470. With the wheels 470, the manipulator 430 is now mobile and is easily movable to integrated circuit wafer probe stations for probing wafers or to device handlers for testing packaged individual chips.

Thus in various embodiments, a weight compensation apparatus connects a test head within an automatic test equipment system to a supporting structure of a manipulator. The weight compensation apparatus includes a mechanism with one or more constant force springs connected to apply a constant upwardly directed force to the supporting structure to offset the weight of the test head to inhibit the test head from moving unless a relatively small external force is applied. The constant force spring(s) have one end wrapped around the freely rotating drum(s) that are attached to the support structure and an opposite end attached to the test head or to the support structure.

In some embodiments, the mechanism to apply an upwardly directed force further includes a device to provide mechanical advantage to multiply the force of the constant force springs applied to compensate the weight of the test head. The device to provide the mechanical advantage includes at least one pulley connected directly to the test head or indirectly increases the mechanical advantage or indirectly to the test head via a support arm. The support arm bears the load of the test head and rests in a guide rail of the supporting structure. Each of the outer ends of the constant force springs are passed through one pulley attached directly to the test head to provide the support for the test head.

In various other embodiments, the drums of FIGS. 3, 4, and 5 (105a and 105b, 206, and 306, respectively) may in fact be a hollow cavity or drum within the supporting structure of FIGS. 3, 4, and 5 (135, 235, and 335, respectively containing the constant force springs 110a and 110b, 207, and 307.

Some embodiments provide that the tandem constant force springs of FIG. 3 105a and 105b may in fact be laminated and mounted on or in a single drum. Also, the two of tandem constant force springs of FIG. 3 105a and 105b are illustrative and any number of constant force springs may be incorporated in the structure and be in keeping with the intent of this invention.

Various other embodiments provide that the pulleys 209 and 309 of FIGS. 4 and 5 are shown as single pulleys. It would be understood by one skilled in the art that the mechanical advantage of multiple pulleys could be configured to multiply the force available for countering the load of the test head 215 and 315 of FIGS. 4 and 5.

In a related embodiment to the embodiment of FIG. 6, a pulley structure similar to that of FIG. 4 or FIG. 5 may be included to provide additional mechanical advantage to multiply the force of the constant force spring 407 of FIG. 6.

An advantage of the constant force spring over a counterbalance weight system of FIG. 2 is that there is less mass in motion to overcome when slowing or stopping a mobile manipulator. The constant force spring(s) allow reduced weight to allow the entire manipulator to be more easily moved as a mobile unit. In the counterbalance weight system of FIG. 2, both the test head and counterbalance weight must be slowed or stopped. With a constant force spring there is only the momentum of the test head and the support structure to bring to rest. Furthermore, there is not the problem of damping typically associated with conventional springs.

While this invention has been particularly shown and described with reference to the embodiments thereof, it will be understood by those skilled in the art that various changes in form and details may be made without departing from the spirit and scope of the invention.

What is claimed is:

1. In an automated test equipment system, a test head weight compensation device comprising at least one constant force spring connected between a test head assembly of the automated test equipment system and a test head supporting structure for applying to the test head assembly along a full range of vertical travel of the test head assembly a constant supportive force having substantially a same magnitude and opposite direction as a weight of the test head assembly.

2. The test head weight compensation device of claim 1, wherein the at least one constant force spring is rotatably mounted to the supporting structure with a distal end of the at least one constant force spring is attached to the test head assembly.

3. The test head weight compensation device of claim 1, further comprising at least one pulley connected to the test head assembly, and wherein the at least one constant force spring is rotatably mounted to the support structure and passes through the at least one pulley with a distal end connected to the supporting structure.

4. The test head weight compensation device of claim 3 wherein the distal end of the at least one constant force spring is attached to the supporting structure.

5. The test head weight compensation device of claim 4 wherein the at least one pulley is attached to a test head support arm of the test head assembly.

6. The test head weight compensation device of claim 1 wherein the at least one constant force spring is rotatably mounted to the test head assembly with a distal end of the at least one constant force spring connected to the supporting structure.

7. The test head weight compensation device of claim 1 further comprising at least one pulley connected to the supporting structure, and wherein the at least one constant force spring is mounted to the test head assembly and passes through the at least one pulley with a distal end of the at least one constant force spring connected to the test head assembly.

8. In automatic test equipment systems, a manipulator for supporting and orienting a test head, the manipulator comprising a weight compensation device connected between the test head and a supporting structure of the manipulator for applying an upwardly directed constant force along a range vertical motion of the test head to offset the weight of the test head, the weight compensation device comprising at least one constant force spring mounted to the supporting structure and having a distal end connected to support the test head and so as to substantially reduce a force necessary to overcome an inertia of the test head.

9. The manipulator of claim 8, wherein a distal end of the at least one constant force spring is attached to the test head.

10. The manipulator of claim 8, further comprising at least one pulley connected to the test head, the at least one constant force spring passing through the at least one pulley to multiply the force of the constant force spring applied to compensate the weight of the test head.

11. The manipulator of claim 10, wherein a distal end of the at least one constant force spring is attached to the support structure.

12. The manipulator of claim 11 wherein the at least one pulley is attached to a support arm, the support arm bearing the test head.

13. The manipulator of claim 12 wherein the support arm rests in a guide rail of the supporting structure.

14. The manipulator of claim 8 further comprising wheels mounted to the manipulator so as to provide a mobile manipulator.

15. A mobile test head manipulator capable of supporting and orienting a test head, the manipulator comprising:
 a) at least one constant force spring connected between a test head assembly and a test head supporting structure for applying to the test head assembly along a range of vertical travel of the test head assembly a constant supportive force having substantially a same magnitude and opposite direction as a weight of the test head assembly; and
 b) wheels secured to a base of the manipulator.

16. The mobile test head manipulator of claim 15, wherein the at least one constant force spring is mounted to the supporting structure with a distal end of the at least one constant force spring is attached to the test head assembly.

17. The mobile test head manipulator of claim 15, further comprising at least one pulley connected to the test head assembly, and wherein the at least one constant force spring is mounted to the test head supporting structure and passes through the at least one pulley with a distal end connected to the test head supporting structure.

18. The mobile test head manipulator of claim 17, wherein the distal end of the at least one constant force spring is attached to the test head supporting structure.

19. The mobile test head manipulator of claim 18, wherein the at least one pulley is attached to a support arm of the test head assembly, the support arm bearing the test head.

20. The mobile test head manipulator of claim 19, wherein the test head support arm of the test head assembly rests in a guide rail of the test head supporting structure.

21. The mobile test head manipulator of claim 15, wherein the constant force spring is mounted to the test head assembly and the distal end is connected to the test head supporting structure.

22. The mobile test head manipulator of claim 21 further comprising at least one pulley connected to the test head supporting structure, and wherein the at least one constant force spring is mounted to the test head and passes through the at least one pulley with a distal end of the at least one constant force spring connected to the test head assembly.

* * * * *